United States Patent
Aklog et al.

(10) Patent No.: US 8,956,383 B2
(45) Date of Patent: Feb. 17, 2015

(54) DEVICES AND METHODS FOR REMOVING CLOTS

(75) Inventors: Lishan Aklog, Scottsdale, AZ (US); Michael Glennon, Norwell, MA (US)

(73) Assignee: ArgioDynamics, Inc., Latham, NY (US)

(*) Notice: Subject to any disclaimer, the term of this patent is extended or adjusted under 35 U.S.C. 154(b) by 98 days.

(21) Appl. No.: 13/310,201

(22) Filed: Dec. 2, 2011

(65) Prior Publication Data

US 2012/0143239 A1 Jun. 7, 2012

Related U.S. Application Data

(60) Provisional application No. 61/419,378, filed on Dec. 3, 2010.

(51) Int. Cl.
| | | |
|---|---|---|
| A61M 29/00 | (2006.01) | |
| A61B 17/3207 | (2006.01) | |
| A61B 17/22 | (2006.01) | |
| A61B 17/221 | (2006.01) | |

(52) U.S. Cl.
CPC ....... *A61B 17/3207* (2013.01); *A61B 17/22032* (2013.01); *A61B 2017/22062* (2013.01); *A61B 2017/2215* (2013.01); *A61B 2017/320716* (2013.01)
USPC ........................................ 606/200

(58) Field of Classification Search
CPC .................. A61F 2002/018; A61F 2230/0006; A61F 2/013; A61F 2250/0003; A61F 2230/0067; A61F 2230/008; A61F 2/01; A61F 2002/30092; A61F 2210/0014
USPC ......... 606/110, 112, 114, 127, 191, 194, 198, 606/200; 604/101.01, 101.04, 101.05, 604/103.06, 103.13, 103.14, 28
See application file for complete search history.

(56) References Cited

U.S. PATENT DOCUMENTS

| | | | |
|---|---|---|---|
| 4,921,478 A | 5/1990 | Solano et al. | |
| 5,908,435 A | 6/1999 | Samuels | |
| 5,964,806 A * | 10/1999 | Cook et al. | 623/11.11 |
| 6,491,712 B1 | 12/2002 | O'Connor | |
| 8,038,704 B2 | 10/2011 | Sherburne | |
| 8,470,016 B2 | 6/2013 | Sherburne | |
| 2006/0041228 A1 | 2/2006 | Vo et al. | |
| 2006/0047300 A1 | 3/2006 | Eidenschink | |
| 2006/0058836 A1* | 3/2006 | Bose et al. | 606/200 |
| 2007/0038241 A1 | 2/2007 | Pal | |
| 2009/0163846 A1* | 6/2009 | Aklog et al. | 604/5.02 |
| 2012/0109179 A1* | 5/2012 | Murphy et al. | 606/194 |

FOREIGN PATENT DOCUMENTS

WO   WO 2010/119110   10/2010

OTHER PUBLICATIONS

International Search Report and Written Opinion based on PCT/US2011/063103 dated Mar. 21, 2012.

* cited by examiner

*Primary Examiner* — Katherine M Shi
(74) *Attorney, Agent, or Firm* — Peter J. Flora

(57) ABSTRACT

A device for capturing a clot is provided. The device can include an inflatable body, a network of veins incorporated thereinto, and a wall defining the inflatable body. The inflatable body can include a pathway substantially axial therethrough upon inflation. The network of veins, upon introduction of a fluid thereinto, can inflate the inflatable body to a predetermined shape. The wall can extend between adjacent veins to define the pathway through the inflatable body and to direct the clot therethrough.

7 Claims, 12 Drawing Sheets

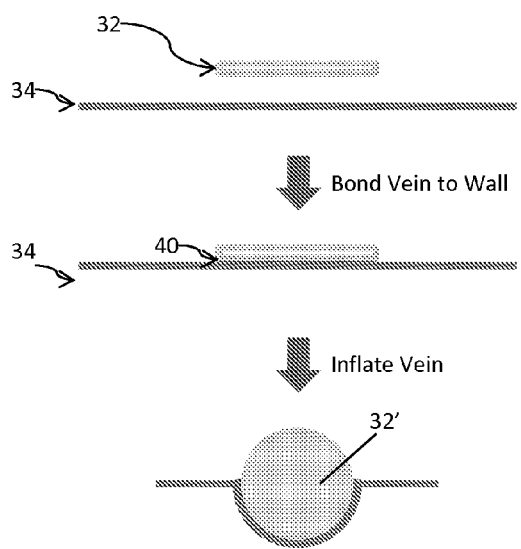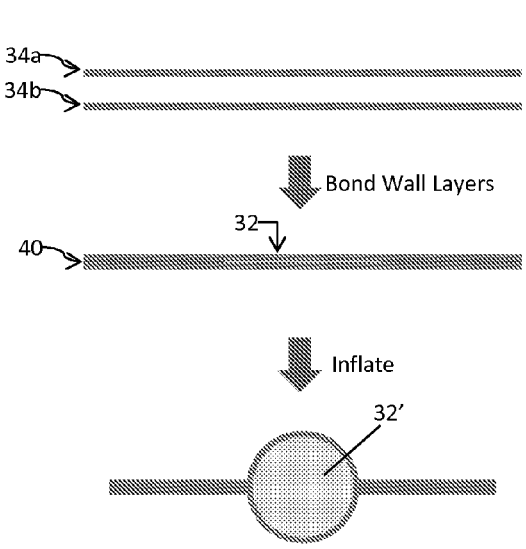

DEVICES AND METHODS FOR REMOVING CLOTS

RELATED APPLICATIONS

This application claims priority to and the benefit of U.S. Provisional Application No. 61/419,378, filed Dec. 3, 2010, the entire teachings of which are incorporated herein by reference.

TECHNICAL FIELD

The present invention relates to devices, systems and methods for removing undesirable materials from a site of interest. More particularly, the present invention relates to devices and methods for removing clots.

BACKGROUND OF THE INVENTION

Many of the most common and deadly diseases afflicting mankind result from or in the presence of undesirable material, most notably blood clots, in the blood vessels and heart chambers. Examples of such diseases include myocardial infarction, stroke, pulmonary embolism, deep venous thrombosis, atrial fibrillation, infective endocarditis, etc. The treatment of some of these conditions, which involve smaller blood vessels, such as myocardial infarction and stroke, has been dramatically improved in recent years by targeted mechanical efforts to remove blood clots from the circulatory system. Other deadly conditions, which involve medium to large blood vessels or heart chambers, such as pulmonary embolism (½ million deaths per year) or deep venous thrombosis (2-3 million cases per year) have not benefited significantly from such an approach. Present treatment for such conditions with drugs or other interventions is not sufficiently effective. As a result, additional measures are needed to help save lives of patients suffering from these conditions.

The circulatory system can be disrupted by the presence of undesirable material, most commonly blood clots, but also tumor, infective vegetations, and foreign bodies, etc. Blood clots can arise spontaneously within the blood vessel or heart chamber (thrombosis) or be carried through the circulation from a remote site and lodge in a blood vessel (thromboemboli).

In the systemic circulation, this undesirable material can cause harm by obstructing a systemic artery or vein. Obstructing a systemic artery interferes with the delivery of oxygen-rich blood to organs and tissues (arterial ischemia) and can ultimately lead to tissue death or infarction. Obstructing a systemic vein interferes with the drainage of oxygen-poor blood and fluid from organs and tissues (venous congestion) resulting in swelling (edema) and can occasionally lead to tissue infarction.

Many of the most common and deadly human diseases are caused by systemic arterial obstruction. The most common form of heart disease, such as myocardial infarction, results from thrombosis of a coronary artery following disruption of a cholesterol plaque. The most common causes of stroke include obstruction of a cerebral artery either from local thrombosis or thromboemboli, typically from the heart. Obstruction of the arteries to abdominal organs by thrombosis or thromboemboli can result in catastrophic organ injury, most commonly infarction of the small and large intestine. Obstruction of the arteries to the extremities by thrombosis or thromboemboli can result in gangrene.

In the systemic venous circulation, undesirable material can also cause serious harm. Blood clots can develop in the large veins of the legs and pelvis, a common condition known as deep venous thrombosis (DVT). DVT arises most commonly when there is a propensity for stagnated blood (long-haul air travel, immobility) and clotting (cancer, recent surgery, especially orthopedic surgery). DVT causes harm by (1) obstructing drainage of venous blood from the legs leading to swelling, ulcers, pain and infection and (2) serving as a reservoir for blood clot to travel to other parts of the body including the heart, lungs (pulmonary embolism) and across a opening between the chambers of the heart (patent foramen ovale) to the brain (stroke), abdominal organs or extremities.

In the pulmonary circulation, the undesirable material can cause harm by obstructing pulmonary arteries, a condition known as pulmonary embolism. If the obstruction is upstream, in the main or large branch pulmonary arteries, it can severely compromise total blood flow within the lungs and therefore the entire body, resulting in low blood pressure and shock. If the obstruction is downstream, in large to medium pulmonary artery branches, it can prevent a significant portion of the lung from participating in the exchange of gases to the blood resulting low blood oxygen and build up of blood carbon dioxide. If the obstruction is further downstream, it can cut off the blood flow to a smaller portion of the lung, resulting in death of lung tissue or pulmonary infarction.

The presence of the undesirable material within the heart chambers can cause harm by obstructing flow or by serving as a reservoir for emboli to other organs in the body. The most common site for obstruction within the heart is in the heart valves. Infective vegetations, a condition known as endocarditis, can cause partial obstruction to flow across a valve before destroying the valve. Patients with prosthetic valves, especially mechanical valves, are particularly prone to valve thrombosis and obstruction. The heart chambers are the most common source of emboli (cardioemboli) to the systemic circulation, including stroke. Emboli tend to arise from areas that are prone to stagnation of blood flow under pathologic conditions. The left atrial appendage in patients with atrial fibrillation is prone to thrombosis, as well as the left ventricular apex in patients with acute myocardial infarction or dilated cardiomyopathy. Infected vegetations or thrombi on the heart valves are also common sources of emboli. Undesirable material such as blood clots and infected vegetations can reside in the chambers of the right heart (atrium and ventricle), often associated with prosthetic material such as pacemaker leads or long-term indwelling catheters.

The most effective treatment for conditions resulting from the presence of blood clots or other undesirable materials within the circulation is, of course, to stabilize or eliminate the material before it has embolized. Alternatively, if obstruction to flow has already occurred but before the obstruction has caused permanent harm (infarction, shock, death), the material can be eliminated by utilizing biologic or mechanical means.

Biologic treatments involve the delivery of agents to the material, which either dissolve the material or, at a minimum, stabilize it until the body can eliminate it. In the case of infective vegetations, antimicrobial agents can, over time, decrease the chances of embolization. In the case of blood clots, the agents include 1) anticoagulant agents (heparin, warfarin, etc.) which prevent propagation of blood clots; and 2) more potent thrombolytic agents (streptokinase, urokinase, tPA, etc.) which actively dissolve clots. The agents are usually delivered systemically, i.e., into a peripheral or central vein and allowed to circulate throughout the body. Thrombolytic agents can also be delivered through a catheter directly to the blood clot which can increase its effectiveness by increasing local concentrations but this does not completely eliminate the absorption into systemic circulation throughout the body.

Thrombolytic agents have been shown to increase survival in patients with hemodynamically significant pulmonary embolism as documented by echocardiographic evidence of right ventricular strain. The use of thrombolytic agents is the standard of care in this subgroup of patients with a high 20-25% early mortality. They are commonly used in to dissolve clots in other blood vessels including arteries to heart, abdominal organs and extremities.

There are two primary disadvantages to thrombolytic agents. First, every cell in the body is exposed to the agent which can lead to serious and often life threatening bleeding complications in remote areas such as the brain and stomach. The risk of major bleeding complications can be as high as 25% and the risk of often fatal bleeding into the brain can go up to 3%. Second, blood clots undergo a process called organization where the soft gel-like red/purple clot is transformed into a firmer, whitish clot by the cross-linking of proteins such as fibrin. Organized clots are much less amenable to treatment with thrombolytic agents. Thromboemboli, such as pulmonary emboli, can contain a significant amount of organized clot since the thrombus frequently developed at its original site (e.g., the deep veins of the legs) over a long period of time prior to embolizing to the remote site (e.g., the lungs).

Mechanical treatments involve the direct manipulation of the material to eliminate the obstruction. This can involve aspiration, maceration, and compression against the vessel wall, or other types of manipulation. The distinct advantage of mechanical treatment is that it directly attacks the offending material and eliminates the vascular obstruction independent of the specific content of the offending material. Mechanical treatments, if feasible, can usually prove to be superior to biologic treatments for vascular obstruction. Procedural success rates tend to be higher. The best example of this advantage is in the treatment of acute myocardial infarction. Although thrombolytic therapy has had a major impact on the management of patient with myocardial infarction, this option is now relegated to a distant second choice. The clear standard of care today for an acute myocardial infarction is an emergency percutaneous coronary intervention during which the coronary artery obstruction is relieved by aspiration, maceration or balloon compression of the offending thrombus. This mechanical approach has been shown to decrease the amount of damaged heart tissue and improve survival relative to the thrombolytic biological approach.

Mechanical treatment, however, has played a limited role in the removal of blood clots found in larger blood vessels such as pulmonary arteries and heart chambers. Surgical pulmonary embolectomy involves opening the pulmonary artery and removing the offending clot under direct vision. This operation has been performed for nearly 100 years, but did not become practical until the introduction of the heart lung machine. Even then, it was generally relegated to a salvage procedure in moribund patients in whom all other options had been exhausted because of the inherent danger in the surgery and the recovery period. While surgical pulmonary embolectomy is very effective in completely evacuating pulmonary emboli whether soft-fresh and firm-organized clot, it is an invasive procedure.

Recent data has shown that the early outcomes with surgical pulmonary embolectomy are excellent, at least as good as thrombolytic treatment, as long as the procedure is performed in a timely fashion before the patient becomes very ill or suffers a cardiac arrest. The long term outcomes of patients surviving surgical pulmonary embolectomy have always been very good. Although these data have generated a renewed interest in performing surgical pulmonary embolectomy, its use remains limited because of the invasiveness of the procedure. Although minimally invasive approaches have been described, the standard procedure requires a 20-25 cm incision through the sternal bone and placing the patient on cardiopulmonary bypass (the heart-lung machine).

Catheter-based removal of blood clots from larger blood vessels (e.g., pulmonary arteries) and heart chambers has had limited success, at least compared to smaller blood vessels (e.g., coronary arteries). Catheter pulmonary embolectomy, where the pulmonary emboli are removed percutaneously using one of several techniques, has been around for nearly 30 years but few patients currently receive these therapies. These techniques can be subdivided into three categories. With fragmentation thrombectomy, the clot is broken into smaller pieces, most of which migrate further downstream, decreasing the central obstruction but resulting in a "no-reflow" phenomenon. It is sometimes used in combination with thrombolytics which preclude their use as an alternative to thrombolytics. With the rheolytic thrombectomy, high velocity saline jets create a Venturi effect and draw the fragments of the clot into the catheter. Finally the aspiration techniques draw the clot into a catheter via suction. With a Greenfield embolectomy, the catheter with the attached clot is repeatedly drawn out of the vein. All of these techniques rely on catheters which are small compared to the size of the clots and blood vessels. Their limited success is likely related to their inability to achieve a complete en-bloc removal of the material without fragmentation.

The experience with catheter-based treatment of deep venous thrombus has also had limited success. The operator must use relatively small catheters to remove or break up large amounts of well embedded clot. This procedure is therefore time-consuming, inefficient and ultimately not very effective in removal of the whole clot.

It is clear that all of the therapeutic options available to patients with clot or other undesirable material in medium or large blood vessels, such as those with pulmonary embolism, have serious limitations. Anticoagulation only limits propagation of clot, but does not remove it. Thrombolytic therapy is not targeted, carries a real risk of major bleeding, and is not very effective in firm/organized clots. Catheter embolectomy uses technology developed for small blood vessels, does not scale well to material residing in medium and large vessels or heart chambers, and thus is not very effective. Surgical embolectomy is highly effective but highly invasive. There is a real need for a direct mechanical treatment that is as effective as surgical embolectomy but can be performed using endovascular techniques.

Current efforts to apply existing catheter embolectomy technologies to medium to large blood vessels and heart chambers encounter at least two obstacles: fragmentation and excessive blood loss. Techniques which depend on fragmentation of the material tend to be inefficient and ineffective in medium to large blood vessels and heart chambers because the flow of blood will carry a significant portion of the fragmented material away before it can be captured in the catheter. On the other hand, techniques which depend on aspiration of undesirable material will result in excessive blood loss as the size of the catheter increases.

A need therefore exists for a device and method to endovascularly remove undesirable material residing in medium to large blood vessels and heart chambers with minimal fragmentation and without excessive blood loss.

SUMMARY OF THE INVENTION

The present invention relates generally to devices and methods for removing undesirable material residing in vessels, such as blood vessels, or within chambers of the heart. More specifically, the subject invention relates to devices and methods for using a funnel to remove substantially en bloc, from a site of obstruction or interest, an undesirable material, such as blood clots, embolisms and thromboembolisms, without significant fragmentation and without excessive fluid loss. For example, the devices and methods of the present invention can be used in connection with a cannula (e.g., AngioVac®, Vortex Medical Inc., see allowed U.S. Patent Application Publication No. US2009/0163846 which is to be issued as U.S. Pat. No. 8,075,510) and/or other en bloc systems to remove blood clots. The subject invention can be particularly useful for, but not limited to, the removal of blood clots, tumors, infective vegetations and foreign bodies from medium to large blood vessels and heart chambers.

In one aspect, the subject invention features a device for capturing a clot. The device can include an inflatable body, a network of veins, and a wall defining the inflatable body. The inflatable body can include an entry end, an exit end, and a pathway extending substantially axially through the inflatable body upon inflation. The exit end can be designed to engage a distal end of a cannula. The network of veins can be incorporated into the inflatable body and upon introduction of a fluid thereinto, can inflate the inflatable body to a predetermined shape. The wall extends between adjacent veins to define the pathway through the inflatable body and to direct the clot therethrough. In certain embodiments, the inflatable body is substantially frustoconical in shape upon inflation. The inflatable body can also be substantially tubular upon inflation. The network of veins can be interconnected or separated as individual veins. The veins can be positioned on a surface of the wall or defined between two wall layers. The wall can be substantially inelastic or semi-elastic to maintain the inflatable body in the predetermined shape upon inflation. In some embodiments, the device can further include an elastic sheath for maintaining the inflatable body in a collapsed state before inflation.

In a further aspect, a kit for capturing a clot is provided. The kit can include the device as disclosed herein and a coupling mechanism for engaging the exit end of the device and the distal end of the cannula. The coupling mechanism can provide substantially fluid-tight communication between the pathway of the device and the cannula. The coupling mechanism may be an adhesive or a mechanical component, or any other coupling technique or device known in the art.

In another aspect, the subject invention features a method for capturing a clot. In some embodiments, an inflatable body having a network of veins incorporated thereinto is provided. The inflatable body can be positioned at a site of interest adjacent to a clot. A fluid can be introduced into the network of veins to inflate the inflatable body to a predetermined shape that has an entry end, an exit end, a pathway extending substantially axially therethrough. The clot can be directed through the pathway from the entry end to the exit end. In certain embodiments, in the providing step, the veins can be interconnected or separated. In some embodiments, in the providing step, the veins can be positioned on a surface of a wall which extends between adjacent veins to define a pathway through the inflatable body and to direct the clot therethrough. The wall can be substantially inelastic or semi-elastic to maintain the inflatable body in the predetermined shape upon inflation. In certain embodiments, in the providing step, the veins can be defined between two wall layers. In some embodiments, in the introducing step, the inflatable body can be substantially frustoconical or substantially tubular upon inflation. In one embodiment, the method can further include, before the introducing step, removing an elastic sheath situated about the inflatable body for maintaining the inflatable body in a collapsed state before inflation. In certain embodiment, the method can further include engage the exit end with a distal end of a cannula, to provide substantially fluid-tight communication between the pathway and the cannula.

In yet another aspect, a method for capturing a clot is featured. The method includes positioning the device disclosed herein at a site of interest adjacent to a clot; introducing a fluid into the network of veins to inflate the inflatable body to the predetermined shape; and directing the clot through the pathway.

Also featured in the present invention is use of the device or kit disclosed herein, for the treatment of a disease involving removal of a clot, such as myocardial infarction, stroke, pulmonary embolism, deep venous thrombosis, atrial fibrillation, and infective endocarditis. These and other features and advantages of the present invention will become more apparent from the following description taken in conjunction with the accompanying drawings wherein like reference characters denote corresponding parts throughout the several views.

BRIEF DESCRIPTION OF THE DRAWINGS

FIGS. 2A-2D illustrate two designs for making and using the funnel shown in FIGS. 1A-1G.

DETAILED DESCRIPTION OF SPECIFIC EMBODIMENTS

As noted above, existing catheter techniques may not be effective in removing undesirable material, such as clots, from medium and large size blood vessels or from heart chambers, because these catheters tend to be small relative to the material to be removed. As a result, the material often needs to be fragmented in order to fit within the catheter. However, with fragmentation, the chances of the fragments being carried away in the bloodstream increases, resulting in downstream obstruction. If the catheter is enlarged to accommodate the larger structure and material, such a catheter may aspirate an unacceptable volume of blood, resulting in excessive fluid loss and/or shock in the patient.

The present invention overcomes the deficiencies of existing devices and techniques and allows for capture of undesirable material (e.g., Undesirable Intravasular Material or UIM) while minimizing any fragments that can bypass the catheter. The present invention can be used to capture and remove substantially en bloc (i.e., wholly or entirely) undesirable material, such as thrombi and emboli, from the vasculature, including medium to large size blood vessels, and from heart chambers. The devices and methods of the present invention can be used in connection with any en bloc system to remove clots or other undesirable materials. It should also be appreciated that the present invention can also be used to capture and remove fragments of undesirable material that may be fragmented before or during the capturing and removal process.

Vessels from which the undesirable material can be removed, in accordance with an embodiment of the present invention, include, for example, those within the pulmonary circulation (e.g., pulmonary arteries), systemic venous circulation (e.g., vena cavae, pelvic veins, leg veins, neck and arm veins) or arterial circulation (e.g., aorta or its large and medium branches). The heart chambers can be, for example, in the left heart (e.g., the left ventricular apex and left atrial appendage), right heart (e.g., right atrium and right ventricle), or on its valves. The present invention can also act to remove tumors, infective vegetations and other foreign materials.

Although reference is made to medium and large vessels, it should be appreciated that the systems and methods, hereinafter disclosed, can be scaled and adapted for use within smaller vessels within the body, if desired. In addition, although references are made in connection with surgical protocols, it should be appreciated that the systems and methods of the present invention can be adapted for use in connection with non-surgical protocols, and in connection with any vessel capable of permitting fluid flow therethrough and capable of being obstructed. For instance, the system of the present invention can be adapted for use in connection with clearing obstructed oil pipelines, water pipes, and air ducts, among others.

Figure 1A:
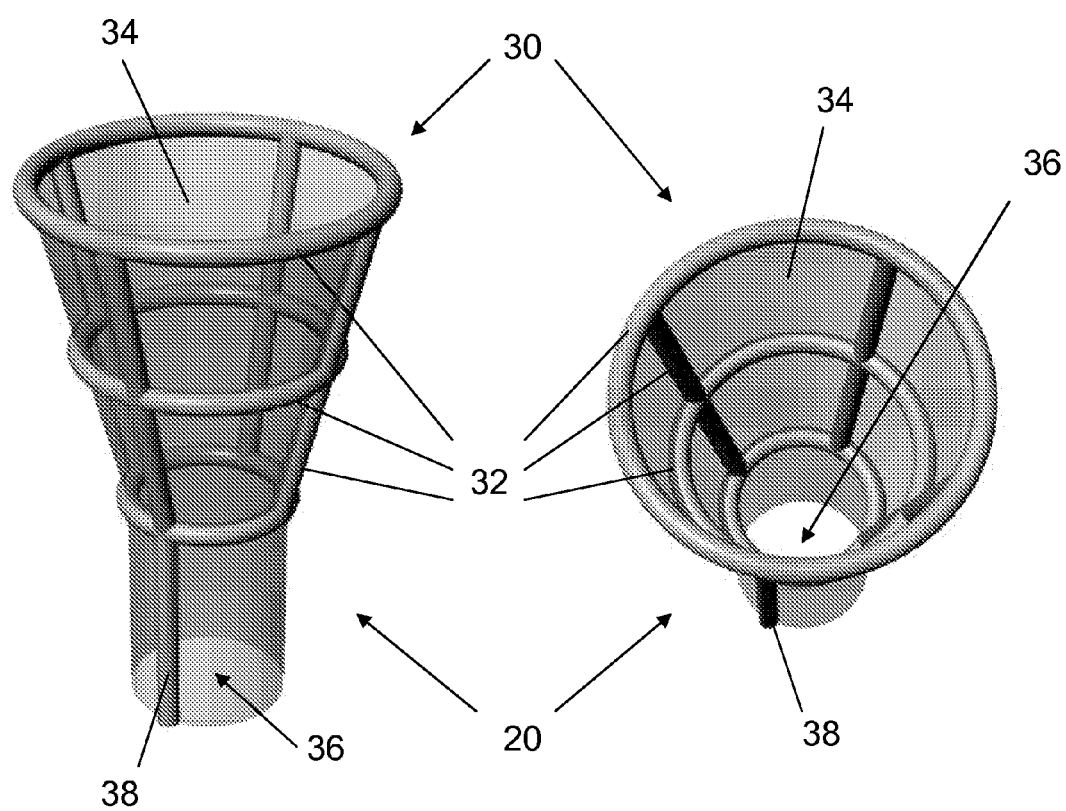
FIGS. 1A-1G illustrate a variety of designs for a funnel in accordance with one embodiment of the present invention.

Referring now to FIG. 1A, there is illustrated a funnel 20 for use in connection with a system for removing an undesirable material, substantially en bloc, from an obstruction site or site of interest, such as those disclosed in allowed U.S. Patent Application Publication No. US2009/0163846 (to be issued as U.S. Pat. No. 8,075,510), the contents of which are hereby incorporated by reference in its entirety. The funnel 20, in an embodiment, can include an inflatable body 30, a network of veins 32, and a wall 34 situated circumferentially substantially about the inflatable body 30. The inflatable body 30, before inflation, can be in a substantially collapsed state. For example, the inflatable body 30 can collapse to a profile having a cross section that may be less than, for example, the size of a cannula, such that the inflatable body 30, in its collapsed state, can be fitted within the cannula, or delivered through the cannula to a site of interest. The inflatable body 30, in an embodiment, can have a smooth tapered surface in its collapsed state, thereby enhancing maneuverability and preventing its edges from catching on sheath, valve, chords, vessel wall, etc. The inflatable body 30 can also have an atraumatic tip substantially free of sharp edges that can cause dissection and/or perforation of nearby tissue.

The inflatable body 30, by design, can be inflated to a predetermined shape. In certain embodiments, the predetermined shape can be a substantially flared shape as illustrated in FIG. 1A. Although illustrated to have a predetermined shape that can be substantially frustoconical, it should be appreciated that the inflatable body 30 can be provided with other geometric shape, including tubular. Upon inflation, the inflatable body 30 can include a pathway 36 substantially axially therethrough. In certain embodiments, the inflatable body 30, in its open position can be sufficiently rigid or robust, so as to resist luminal collapse under a predetermined suction pressure. Such rigidity or robustness can also help resist substantial deformation of the inflatable body 30 under radial stress from surrounding tissue (e.g., vessel wall). The inflatable body 30, in certain embodiments, can also resist deformation under longitudinal stress from firm, semi-adherent obstructing material in the vessel, allowing tip to gently dislodge or fragment undesirable material without causing trauma to surrounding tissue (e.g., vessel wall). It should be appreciated that although the inflatable body 30 can be substantially rigid, to the extent desired, the inflatable body 30 can also have sufficient flexibility and/or elasticity, so that the inflatable body 30 can conform to, for example, the shape of the vessel and vessel wall in which the inflatable body 30 is being deployed.

In use, undesirable materials (e.g., blood clots) can be directed through the pathway 36 of the inflatable body 30, and be passed into the cannula. After use/deployment, the inflatable body 30 can be deflated, recollapse, and return to smooth tapered surface. In this way, there is no need to remove or reposition the inflatable body 30.

Inflation and/or deflation of the inflatable body 30 can be achieved via the network of veins 32 incorporated thereinto. The veins 32 can be a network of small caliber channels in thin walled structure to form ribbed scaffolding. In an embodiment, a port 38 can be provided and can be in fluid communication with the veins 32 for introducing a fluid thereinto. Suitable fluid can include gas, liquid, and/or radioopaque contrast material. Upon introduction of the fluid, the empty veins 32 can be inflated to a predetermined size and/or shape, depending on the inflation pressure and the vein material. In some embodiments, the fluid in the veins 32 can provide sufficient support so that the inflatable body 30 can be inflated to a predetermined shape.

Veins 32, in an embodiment, can be made from inelastic or semi-inelastic materials so that they can withstand the pressure from the fluid and can be sufficiently rigid or semi-rigid when pressurized. In addition, veins 32 can be made from a sufficiently stiff material or can be reinforced with a sufficiently stiff material, so as to not collapse significantly under a suction force. In one embodiment, veins 32 can be constructed from a biocompatible material, such as polyvinyl chloride, polyethylene, polypropylene, polyurethane, Pebax®, silicone, or a combination thereof.

Figure 1B:
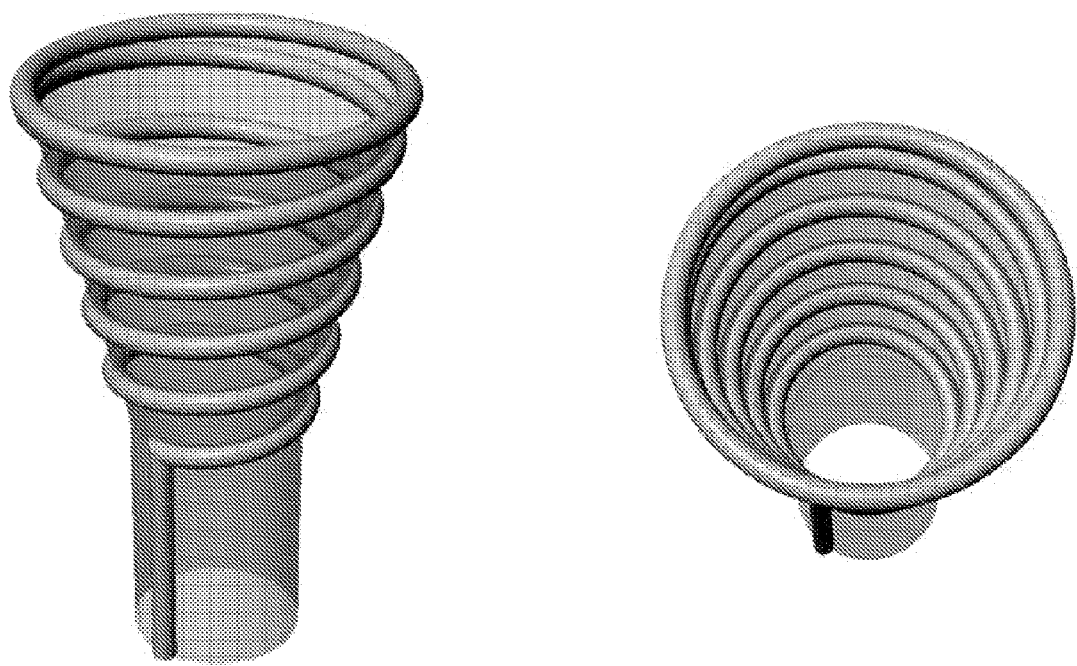
Figure 1C:
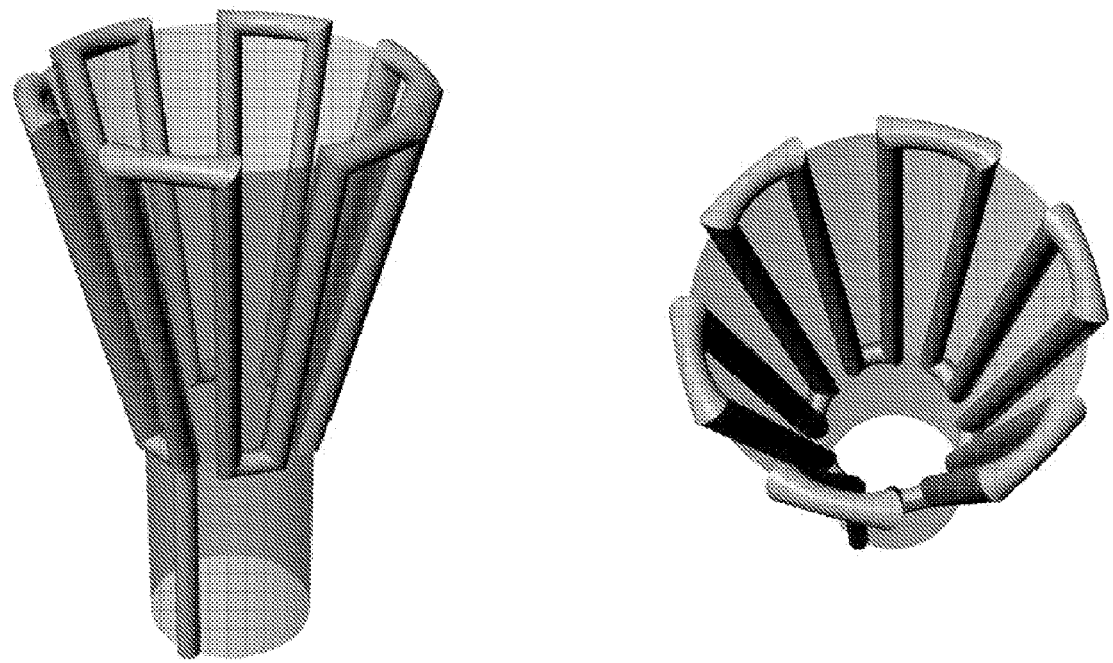
Figure 1D:
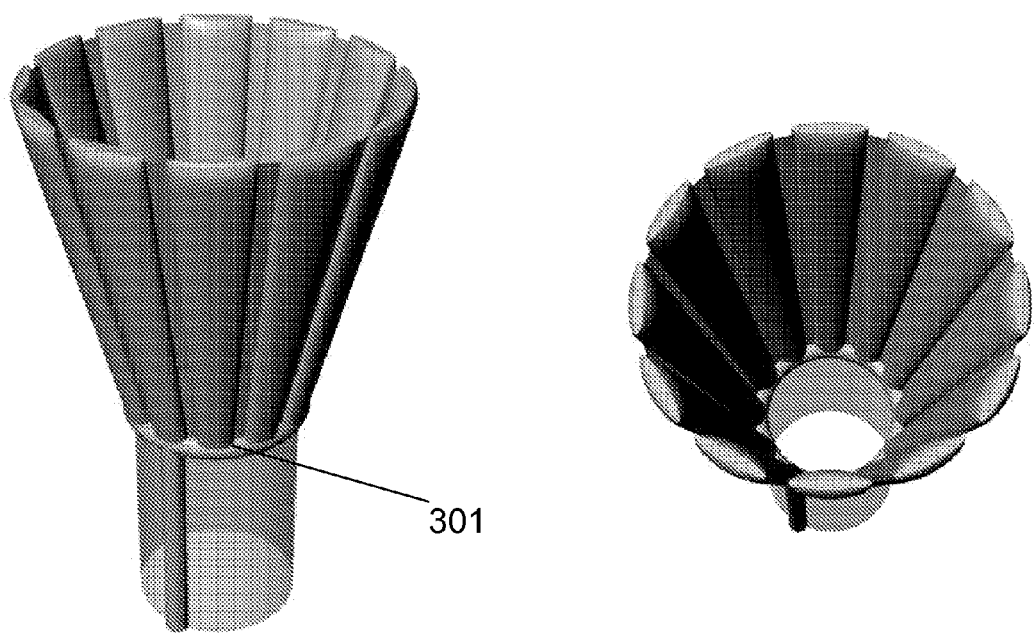
Figure 1E:
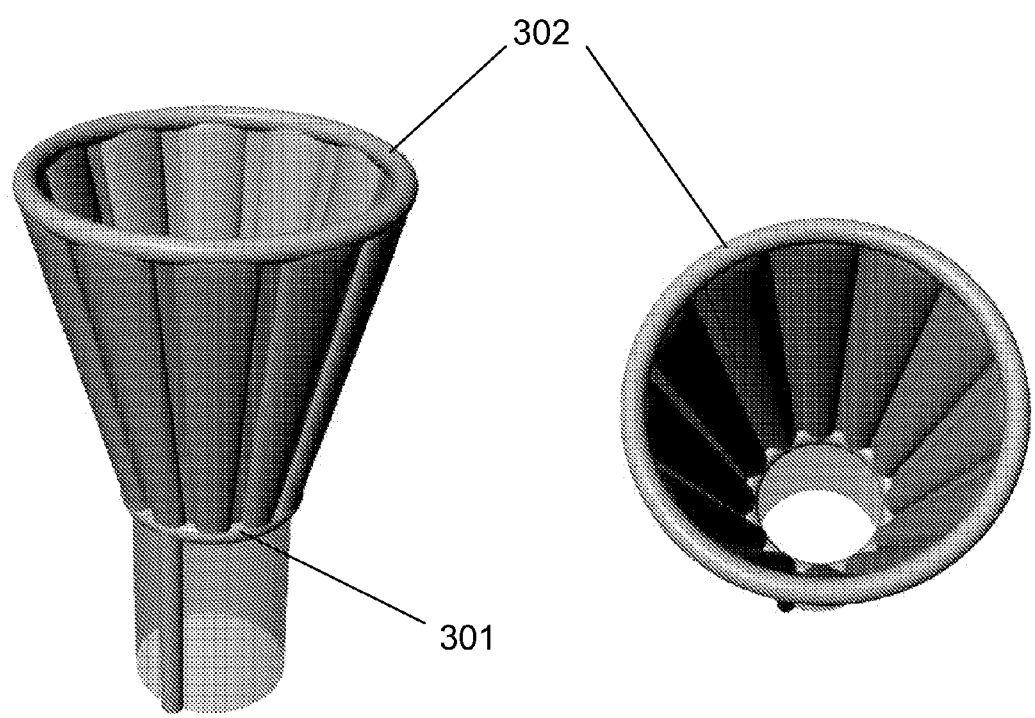
Figure 1F:
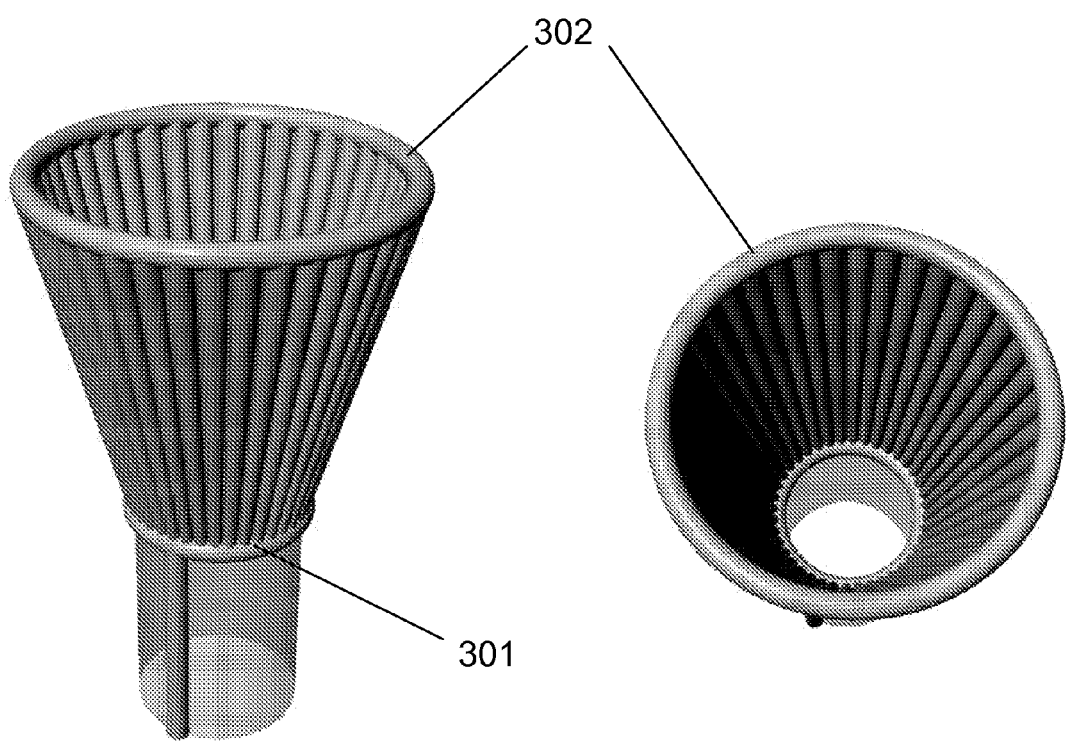

The network of veins 32 can be interconnected (as shown in FIGS. 1A-1C) or separated (as shown in FIGS. 1D-1F), in a variety of designs. For example, the veins 32 can be a continuous channel having one fluid entry point, or have a plurality of separated channels, each having a separate fluid entry point.

The network of veins 32, as shown in FIGS. 1A-1F, can be designed to include hoops (FIG. 1A), spiral (FIG. 1B), zigzag (FIG. 1C), quilt with proximal hoop (FIG. 1D), quilt with proximal and distal hoops (FIG. 1E), corduroy quilt (FIG. 1F), or any combination thereof. For example, the hoops structure of FIG. 1A can include one or more channels where concentric hoops can be connected to one or more longitudinal arms. The hoops geometry/structure may be a complex network with a plurality of intersections, and can be designed in such a way that the structure is sufficiently robust in resisting radial and longitudinal deformation.

The spiral structure of FIG. 1B can include a single channel wound in a helical spiral. The pitch of the spiral can be adjusted to optimize its rigidity, according to type and amount of materials used for the spiral, as well as the desired collapsed size (e.g., smaller than the cannula size). The spiral can include additional supporting material/structure (e.g., substantially inelastic walls) to enhance its rigidity or robustness in resisting longitudinal deformation.

The zigzag structure of FIG. 1C can have a single channel zigzagging from a proximal end to a distal end. The zigzag can be designed to be sufficiently robust in the longitudinal direction. It should also be appreciated that the zigzag structure can be strengthened in the radial direction, for example, by including a supporting material/structure.

The network of veins 32 can, in some embodiments, include the quilt structure of FIGS. 1D-1F. The quilt structure can be formed by partially attaching or bonding two layers of materials, leaving unbonded portions open for use as veins. The bonded segments can be designed to be sufficiently narrow, to maximize the portions for use as veins between layers. The bonded segments can also be designed to have different pattern, size and/or number of veins. The bond should be sufficiently strong to maintain the quilt structure under inflation pressure and/or suction force. In some embodiments, the network of veins can include a proximal hoop 301 (FIGS. 1D and 1E), and/or a distal hoop 302 (FIGS. 1E and 1F). The hoops 301 and 302, by design, can be in fluid communication with the individual veins and supply and/or distribute a fluid thereinto, so as to inflate the network of veins.

The wall 34, in an embodiment, extends between adjacent veins to define the pathway 36 through the inflatable body 30. The wall 34 can also act to direct the clot through the pathway 36 (e.g., by preventing the clot from leaking through spaces between the veins 32). In some embodiments, the wall 34 can be substantially impermeable. Wall material between veins can be a thin membrane. In some embodiments, wall material can be sufficiently flexible or pliable. Wall material can also be substantially inelastic or semi-elastic so as to maintain the inflatable body 30 in the predetermined shape. For example, when veins 32 are empty (e.g., before inflation or after deflation), wall 34 can be substantially flexible or floppy, such that wall 34 can be collapsed down to keep the inflatable body 30 in a desired shape (e.g., tapered, crossing profile). When veins 32 are filled by a fluid (e.g., gas, liquid, radioopaque contrast material, etc.) under pressure, wall 34 can provide sufficient support to the filled veins, thereby creating a substantially rigid or semi-rigid skeleton defined by a predetermined pattern of a venous network of the veins 32.

In accordance with an embodiment of the present invention, any part of the inflatable body 30, the veins 32, and the wall 34 can include a radioopaque material or any material capable of being visualized using fluoroscopy or echocardiography. This can allow visualization of the funnel 20 to facilitate its maneuver, position, and/or deployment under image guidance.

Figure 2C:
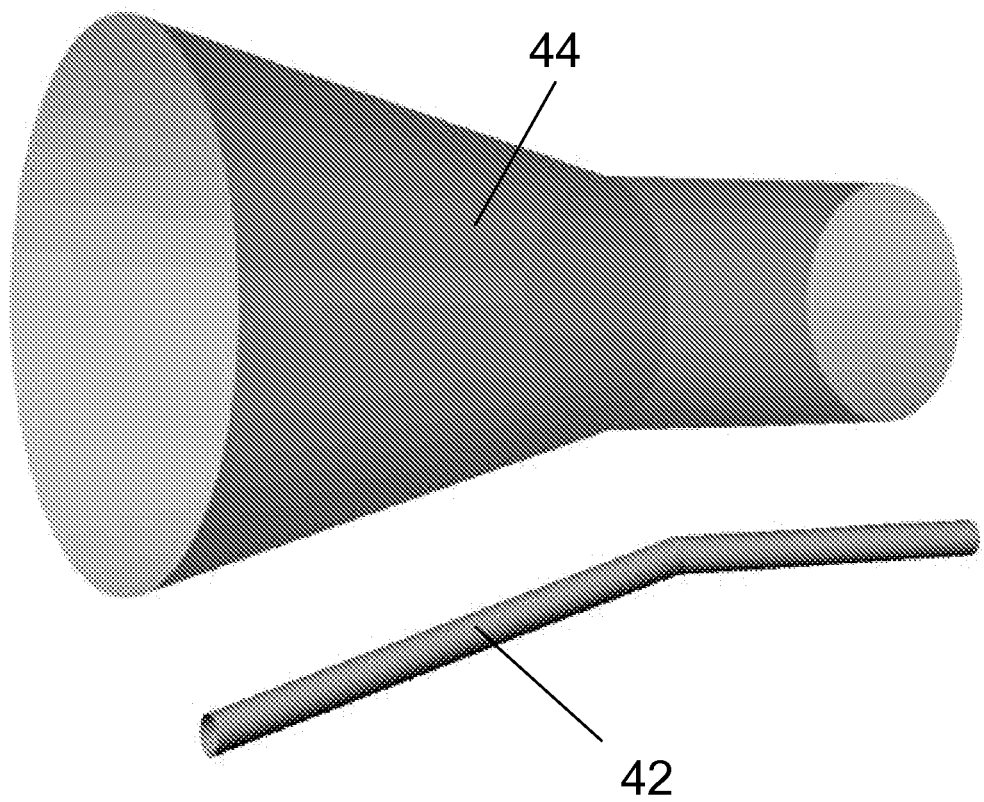
Figure 2D:
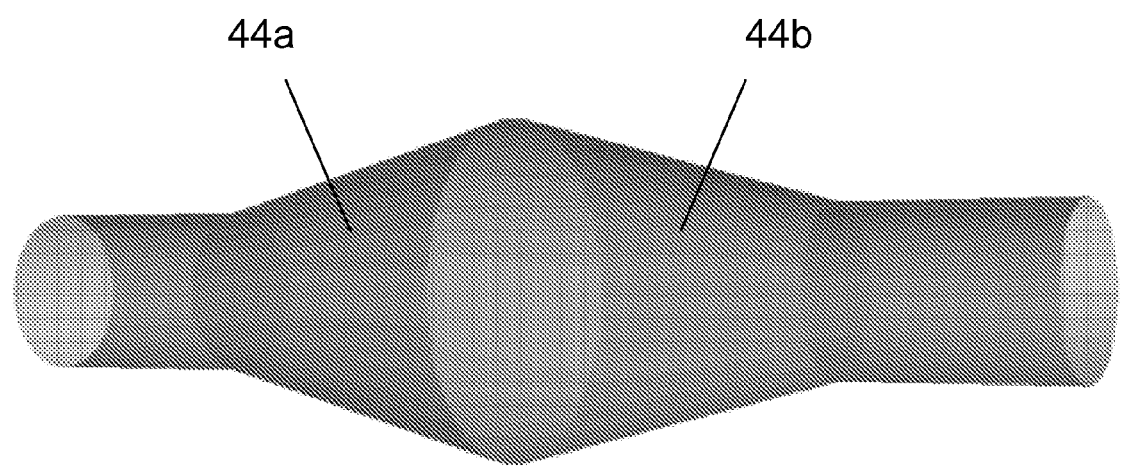

The veins 32 and wall 34 can be constructed in a variety of ways. FIGS. 2A-2D illustrate that the veins 32 can be situated on a surface of the wall 34 (FIGS. 2A and 2C) or defined by two wall layers 34a, 34b (FIGS. 2B and 2D). In either case, upon introduction of a fluid into empty vein 32 (e.g., substantially flat in shape), the inflated vein 32' can change in shape and/or size.

In some embodiments, the funnel of the subject invention can include a single layer of wall material. In the cross section view as shown in FIG. 2A, vein 32 (only one vein shown for illustration purposes) and wall 34 are attached to each other via bond 40. In FIG. 2C, there is illustrated a wall 44 formed in a substantially frustoconical shape. A network of veins can be created by bonding one or more small caliber tubing 42 (only one shown for illustration purposes) to the wall 44 in a predetermined pattern/geometry. Tubing 42 can be bonded to wall 44 by hand or using a machine. Tubing 42 can have different shape (e.g., straight or curved) and/or geometric profile (e.g., round or square), and can have different length and/or size. Wall 44 and tubing 42 can have different physical properties (e.g., elasticity, stiffness, etc.). For example, wall 44 can be inelastic or semi-elastic, minimizing profile of the funnel in its collapsed state. Tubing 42 can be elastic or semi-elastic, so that it can expand upon introduction of a fluid, thereby allowing sufficient amount of fluid to enter.

In another embodiment, the funnel of the subject invention can be made of two layers of wall material. In FIG. 2B, wall layers 34a and 34b can be attached to each other by partially applying bond 40 therebetween, thereby leaving an unbonded space for use as vein 32. For example, wall layers 44a and 44b of FIG. 2D, each formed in a substantially frustoconical shape, can be provided. The wall layers 44a and 44b can be initially sealed at the rims in an opposing relation, and then one layer can be inverted toward or into the other layer, so that the two layers can be in a substantially parallel relation to each other. The network of veins can be created by bonding two wall layers at one or more predetermined position, leaving gaps to form venous channels (e.g., sinusoids). The funnel can be manufactured in an automated or semi-automated fashion with bonding pattern applied by machined part. The two wall layers can be made of the same or different materials. In one embodiment, both wall layers can be inelastic or semi-elastic. In some embodiments, different materials can be pieced together to form a wall, where some parts of the wall can have different physical properties than other parts of the wall. For example, the bonded parts of the wall can be less elastic or more rigid, whereas the unbonded parts (i.e., veins) can be sufficiently elastic.

The attachment or bonding can be accomplished using any methods or mechanisms known in the art. For instance, adhesives, knots, and/or soldering can be used. Bond should be sufficiently strong to prevent layers from peeling apart under pressure. In some embodiments, bond can enhance rigidity of the wall.

The funnel 20, in some embodiments, can be balloon actuated. For example, the funnel 20 can be used with a proximal occluding balloon. In some embodiments, funnel 20 can include a balloon 33 (FIG. 1G) positioned circumferentially about funnel 20 and proximal to cannula. Balloon 33 can be inflated and expand radially, by introducing thereinto a fluid, including water, air, and/or radioopaque contrast material through port 38. Moreover, to the extent desired, balloon 33 can be designed to expand to a diameter larger than that of the vessel within which funnel 20 is being deployed. In that way, funnel 20 can be securely positioned at the site of interest for removal of the undesirable material substantially en bloc.

In certain instances, balloon 33 can act to enhance the suction force being applied at the site of interest when removing the undesirable material. For instance, when funnel 20 and/or cannula is deployed downstream of the undesirable material, rather than substantially adjacent to the undesirable material, within a vessel having a venous circulation (i.e., flow toward the heart), balloon 33, when expanded radially, can substantially occlude the vessel, such that collateral fluid flow within the vessel can be minimized, thereby increasing the suction force that can be applied to the undesirable material. Additionally, the occlusion of such a vessel by balloon 33 can better direct the material being removed into the funnel 20 and prevent the material from being carried by the flow of blood past the funnel.

Alternatively, when funnel 20 and/or cannula is deployed upstream of the undesirable material within a vessel having an arterial circulation (i.e., flow away from the heart), rather than substantially adjacent to the undesirable material, balloon 33, when expanded radially, can substantially occlude the vessel, such that pressure being exerted on the downstream material by the fluid flow can be lessened. By lessening the pressure on the material to be removed, the suction force being applied at the site of interest can act to remove the material more easily.

Figure 3A:
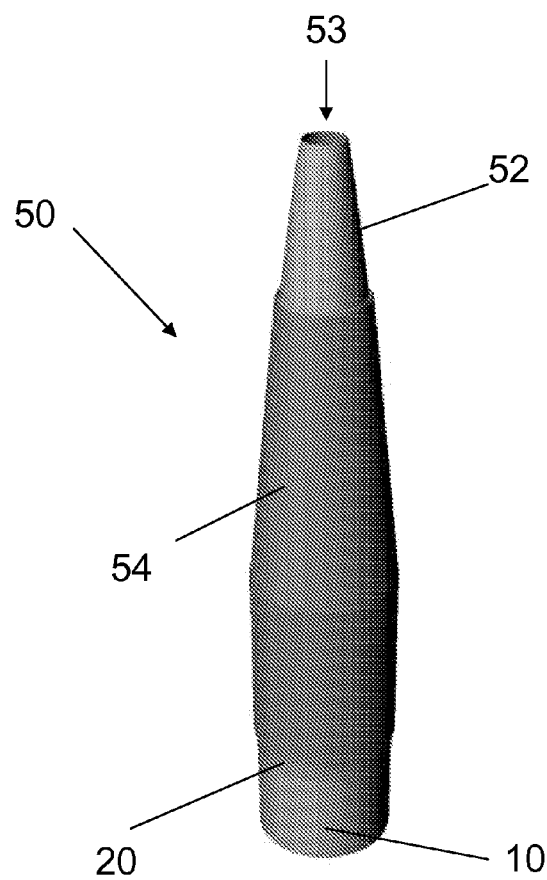
FIGS. 3A-3B illustrate an obturator and sheath for use in connection with the funnel shown in FIGS. 1A-1G.
Figure 3B:
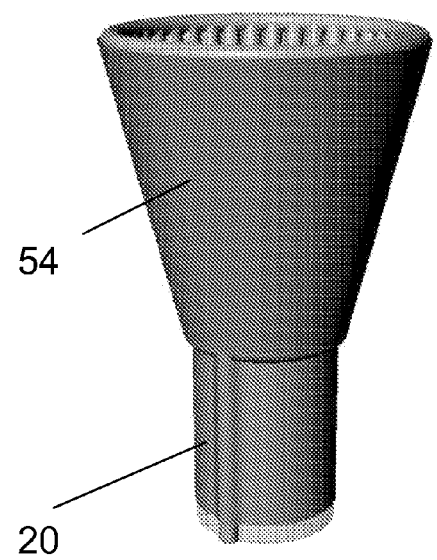

With reference to FIGS. 3A-3B, obturator 52 and/or sheath 54 can be used to facilitate the funnel 20 to maintain a collapsed, tapered state. In that way, funnel 20 along with cannula 10 can be easily advanced along a vessel. Obturator 52 can also act to guide cannula 10. In an embodiment, obturator 52 can be placed substantially axially through funnel 20 (e.g., through the pathway 36) and situated between funnel 20 and cannula 10, thereby forming an assembly 50. Obturator 52 can be substantially frustoconical in shape, and can have a pathway 53 therethrough so that a guide wire (not shown) can be provided through the pathway 53 to help direct the assembly 50 when maneuvering in a vessel. To the extent desired, obturator 52 can be designed to have any desired shape or profile. For example, obturator 52 can have a tapered profile to enhance its maneuverability. In an embodiment, the cross section profile of obturator 52 can be smaller than the cannula 10.

Obturator 52 can be made of any material that is sufficiently rigid, so that obturator 52 does not substantially deform or collapse from the compressive strength of funnel 20 and/or sheath 54. Suitable materials include without limitation to, metal, polyvinyl chloride, polyethylene, polypropylene, polyurethane, Pebax®, silicone, or a combination thereof.

In an embodiment, sheath 54 can be provided circumferentially about the funnel 20 to compress funnel 20 against obturator 52. Sheath 54, funnel 20, and obturator 52, together can be provided with a cross sectional profile that is substantially similar to that of obturator 52. Sheath 54 can also provide, for example, the assembly 50 with a smooth surface and a tapered profile in its collapsed state. Sheath 54 can be a thin walled layer of material having sufficient elasticity. In an embodiment, suitable materials for sheath 54 can have an elastic recoil force high enough to compress funnel 20 against obturator 52. In some instances, the material can sufficiently keep funnel 20 in a collapsed state without using an obturator. Sheath 54, in certain embodiments, may also have an elastic recoil force low enough so as to not impede funnel expansion at a predetermined inflation pressure (e.g., 5-20 atm).

Figure 1G:
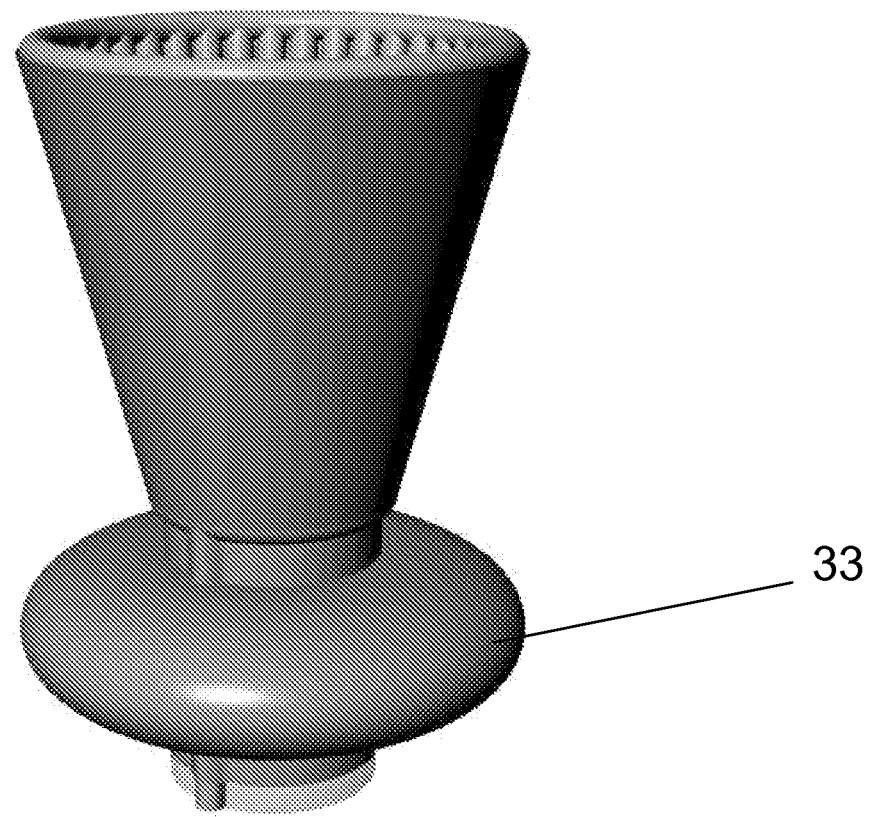

Sheath 54 can be so designed that a portion of the sheath can form an occlusion balloon (see, e.g., FIG. 1G). The balloon can be positioned circumferentially about funnel 20 at its distal end, and can be inflated and expand radially. Moreover, to the extent desired, the balloon can be designed to expand to a diameter larger than that of the vessel within which funnel 20 is being deployed. In that way, funnel 20 can be securely positioned at the site of interest for removal of the undesirable material substantially en bloc.

Obturator 52 and/or sheath 54 can be designed to retract or slide away from the funnel 20. In that way, when the funnel 20 is positioned at the site of interest, and obturator 52 and/or sheath 54 are retracted (e.g., slid away), funnel 20 can be exposed and expanded into the desired shape, as illustrated in FIG. 3B, in order to engage undesirable material.

Figure 4:
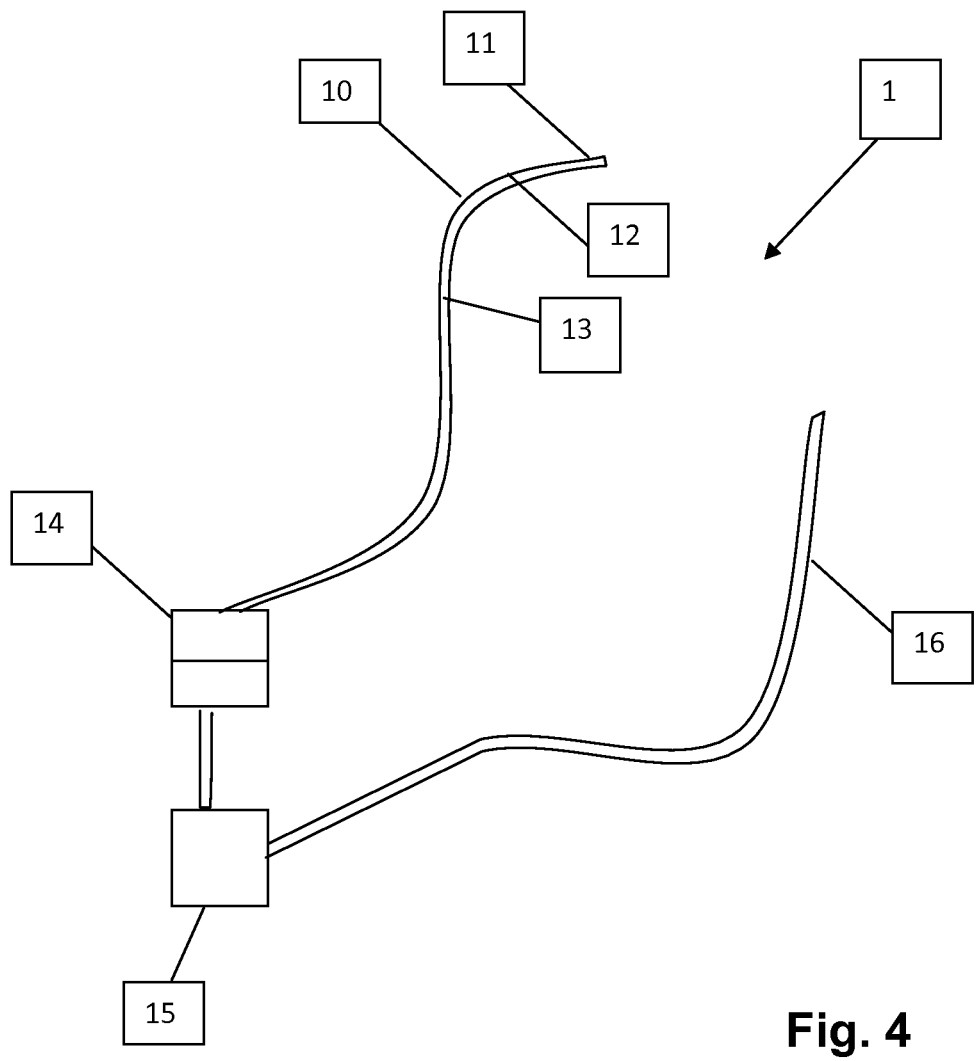
FIG. 4 illustrates a system for removing an undesirable material from within a vessel in accordance with an embodiment of the present invention.

Thus, the present invention features, in one aspect, a funnel for current and future AngioVac® (Vortex Medical Inc.) devices (e.g., FIG. 4, described in U.S. Patent Application Publication No. US2009/0163846, to be issued as U.S. Pat. No. 8,075,510, the contents of which are hereby incorporated by reference in its entirety). The funnel of the present invention improves on existing funnel in terms of performance, versatility, manufacturability, and cost.

Looking now at FIG. 4, system 1 can be used in connection with funnel 20 (not shown) for removing an undesirable material, substantially en bloc, from an obstruction site or site of interest within the vasculature, and for reinfusion of fluid removed (i.e., suctioned or aspirated) from the site of interest back into a patient, in order to minimize fluid loss within the patient. System 1, in an embodiment, may be provided with a first or suction cannula 10 for capturing and removing en bloc the undesirable material from the site of interest, such as that within a blood vessel or a heart chamber. Cannula 10, in an embodiment, may be an elongated tube and may include a distal end 11 through which the undesirable material can be captured and removed. Cannula 10 may also include a lumen or pathway 12 extending along a body portion of cannula 10. Pathway 12, in one embodiment, provides a passage along which the captured material and aspirated circulatory fluid, such as blood, that may be captured therewith may be transported and directed away from the site of interest. Cannula 10 may further include a proximal end 13 in opposing relations to the distal end 11, and through which the captured material may exit from the cannula 10.

System 1 can also include filter device 14 in fluid communication with the proximal end 13 of cannula 10. In some embodiments, system 1 may also be provided with a pump 15 designed to generate negative pressure, so as to create a necessary suction force through cannula 10 to pull any undesirable material from the site of interest. Reinfusion cannula 16, in an embodiment, may be designed to permit filtered fluid, directed from filter device 14 by way of pump 15, to be reinfused back into a patient at a desired site. To that end, reinfusion cannula 16 may be designed for placement within the same or different vessel within which suction cannula 10 may be located.

Since fluid such as blood needs to be filtered through system 1, it should be noted that system 1 and its components can be made from a biocompatible material to minimize any adverse reaction when fluid removed from the site of interest gets reinfused back into the body.

In operation, system 1 of the present invention can be introduced into the vasculature, preferably through a peripheral blood vessel, to remove undesirable material, such as a clot, emboli, or thrombi, substantially en bloc and without significant fragmentation, and subsequently reinfusing fluid removed from the site of interest back into a patient. In particular, system 1 and its components disclosed above can collectively form a substantially closed circuit through which fluid and an undesirable material from a site of interest can be removed by suction, cleared of the undesirable material, filtered to remove any additional debris, and actively introduced back into a patient at a reinfusion site.

In general the method of the present invention, in one embodiment, includes, initially accessing a first blood vessel either by surgical dissection or percutaneously with, for instance, a needle and guide wire. The first blood vessel through which suction cannula 10 can be inserted into patient can be, in an embodiment, any blood vessel that can be accessed percutaneously or by surgical dissection such as femoral vein, femoral artery or jugular vein. Next, suction cannula 10 can be inserted into the first blood vessel over the guide wire, and advanced toward a site of interest, for instance, in a second vessel or a heart chamber where an undesirable material can be residing. The second blood vessel or heart chamber, in an embodiment, can be the main pulmonary artery, branch pulmonary arteries, inferior vena cavae, superior vena cavae, deep veins of the pelvic, legs, arms or neck, aorta, or any other medium to large blood vessel for which the use of a cannula is suitable for removing undesirable material without causing undesirable damage to the blood vessel. In addition, the advancement of suction cannula 10 can be gauged or documented by fluoroscopic angiography, echocardiography or other suitable imaging modality.

In the case of pulmonary embolism, the suction cannula 10 can normally be introduced through the femoral, jugular or subclavian vein. Alternatively, the suction cannula 10 can be introduced, if desired, directly into the cardiac chambers using a minimally invasive surgical or endoscopic, thoracoscopic, or pericardioscopic approach.

Thereafter, a third blood vessel can be accessed either by surgical dissection or percutaneously with, for example, a needle and guide wire. Subsequently, reinfusion cannula 16 can be inserted into the third blood vessel using an open or over the guide wire technique. The third blood vessel through which the reinfusion cannula 16 can be inserted, in one embodiment, can be any large vein, such as the femoral vein or jugular vein. Reinfusion cannula 16 can then be advanced toward a reinfusion site, for example, within a fourth blood vessel. The fourth blood vessel, in one embodiment, can be the femoral vein, iliac vein, inferior vena cava, superior vena cava or right atrium.

Once reinfusion cannula 10 is in place and components of system 1 have connected, pump 15 can be activated, and funnel 20 and suction cannula 10 can then be placed against and in substantial engagement with the undesirable material at the site of interest for removal by suctioning through the suction cannula. The undesirable material and circulatory fluid removed from the site of interest can thereafter be directed along suction cannula 10 into filter device 14 where the undesirable material can be entrapped and removed from the fluid flow. The resulting filtered fluid can next be directed downstream by way of pump 15 into a second filter device, where any debris or material (e.g., ranging from smaller than microscopic in size to relatively larger) that can have escaped and moved downstream from filter device can be further captured and removed from the fluid flow prior to reinfusion. The resulting cleansed fluid can then be directed into the reinfusion cannula 16 and introduced back into the patient.

The method of the present invention can also utilize a suction cannula 10 with a deployable funnel tip, similar to funnel 20 in FIG. 1. In such an embodiment, the funnel 20 can be deployed after suction cannula 10 has been positioned adjacent the site of interest. Thereafter, once the suction force has been activated, the funnel 20 can be advanced to engage the undesirable material for removal. The funnel 20 can remain deployed while the suction force is activated, and through multiple cycles, if necessary, until the undesirable material can be removed. Subsequently, the funnel 20 can recollapse and be retracted in order to reposition or remove suction cannula 10.

For example, the method of the present invention can include providing an inflatable body 30 having a network of veins 32 incorporated thereinto. The inflatable body 30 can be positioned at a site of interest adjacent to a clot. A fluid can be introduced into the network of veins 32 to inflate the inflatable body 30 to a predetermined shape that has a pathway 36 substantially axial therethrough. The clot can be directed through the pathway 36.

It should be appreciated that since funnel 20 and suction cannula 10 can be deployed within any vessel within patient, depending on the procedure, in addition to being placed substantially directly against the undesirable material at the site of interest, funnel 20 and suction cannula 10 can be deployed at a location distant from the site of interest where direct engagement with the undesirable material may not be possible or desired.

In a situation where the funnel 20 and suction cannula 10 are positioned within a vessel exhibiting a venous flow and at a distant location from the undesirable material, it can be desirable to place the distal end of suction cannula downstream of the undesirable material, so that the fluid flow can push the undesirable material from the site of interest into funnel and suction cannula during suction. To the extent there can be some difficulties with suctioning the undesirable material from its location, if necessary, a catheter can be deployed through suction cannula and to the site of interest, where the undesirable material can be dislodged location for subsequent removal.

On the other hand, when funnel 20 and suction cannula 10 are positioned within a vessel exhibiting arterial flow and at a distant location from the undesirable material, it can be necessary to place the distal end of suction cannula 10 upstream of the undesirable material for the purposes of removal, even though the undesirable material must move against the fluid flow in order to enter into funnel 20 and suction cannula 10. In such a situation, since the fluid flow in the vessel tends to exert a pressure against the undesirable material at the site of interest, and thus can make the undesirable material difficult to remove, funnel 20 and/or suction cannula 10 can include a flow occlusion mechanism, similar to balloon 33 shown in FIG. 1G. When expanded radially, the mechanism can substantially occlude the vessel, such that pressure being exerted on the downstream material by the fluid flow can be lessened. By lessening the pressure on the undesirable material to be removed, the suction force being applied at the site of interest can act to remove the material more easily. Again, if necessary, a catheter can be deployed through suction cannula and to the site of interest, where the undesirable material can be dislodged or drawn back into the cannula to facilitate its removal.

The method of the present invention can, in an embodiment, be employed to remove a plurality of undesirable materials, for instance, within the same vessel or its branches, from multiple vessels within the same vascular bed (e.g. left and right pulmonary arteries), from different vascular beds (e.g. pulmonary artery and iliofemoral veins), or a combination thereof. In such an embodiment, after the first undesirable material has been removed, the suction force can be deactivated. The next undesirable material to be removed can then be located, for example, using an appropriate imaging modality. Suction cannula can thereafter be advanced to the location of this second undesirable material, and the suction force reactivated as above until this second undesirable material can be removed. The cycle can be repeated until each undesirable material at the various identified locations has been removed. Once all undesirable material has been removed, an appropriate procedure to prevent the development of or migration of new material, such as placement of an inferior vena cava filter, can be performed.

The method of the present invention can also be employed in combination with a balloon embolectomy catheter or other devices suitable for dislodging clots or other undesirable material from a cannula or a vessel. For example, should an undesirable material be lodged within suction cannula, a balloon catheter can be inserted through, for instance, a side port of suction cannula and advanced past the lodged undesirable material. The balloon catheter can subsequently be inflated distal to the undesirable material. Once inflated, the suction force can be activated and the inflated catheter withdrawn along the suction cannula to dislodge the undesirable material its location of obstruction. In a situation where the undesirable material can be adherent to a vessel wall, or for some other reason cannot be dislodged by simply applying suction to the site of interest, the balloon catheter can be inserted through the side port of suction cannula, advanced past a distal end of cannula, and past the adherent undesirable material. The balloon catheter can then be inflated distal to the undesirable material. Once inflated, the suction force can be activated and the inflated catheter withdrawn along the suction cannula. As it is withdrawn, the balloon catheter can act to drag the undesirable material into suction cannula.

The method of the present invention can further be employed in combination with a distal protection device (not shown), such as a netting device, designed to be positioned downstream of the undesirable material, when removal can be performed within a vessel having arterial flow. In particular, with suction cannula positioned upstream of the undesirable material, the netting device can be inserted through a side port in suction cannula, advanced past the undesirable material to a downstream location. The netting device can then be deployed to an open position approximating the diameter of the vessel. The deployed netting device can then act to entrap any material that can be dislodged from the site of interest and pushed downstream by the fluid flow. In the absence of the netting device, a dislodged material can be pushed downstream and can be lodged in a more life threatening location.

It is evident from the above description that the systems, including the various components, and methods of the present invention can act to remove clots and other types of undesirable material from the circulation, particularly from medium to larger vessels and heart chambers. Important to achieving this includes the ability of the operator to perform substantially en bloc removal of the undesirable material without significant fragmentation from the site of interest. Such a protocol can only be achieved previously with invasive, open surgery. In addition, by providing a system with components to permit aspirated fluid from the site of interest to be reinfused back to the patient, the system of the present invention allows a sufficiently and relatively large suction cannula to be employed for the removal of a relatively large undesirable material in substantially one piece, without fragmentation. Furthermore, by providing a definitive mechanical treatment to the problem, the systems and methods of the present invention provide an attractive alternative to treatments, such as thrombolysis, which may not be an option or can be ineffective for many patients, and which can carry a significant risk of major complications. As such, the systems and methods of the present invention now provide a significant contribution to the field of cardiovascular medicine and surgery, particularly thromboembolic disease.

Devices, systems, and methods of the present invention can be used in connection with various parts and designs of other surgical devices, sytems, and methods for capturing and/or removing clots, for example, as described in U.S. Patent Application Publication No. US2009/0163846 (to be issued as U.S. Pat. No. 8,075,510), the contents of which are hereby incorporated by reference in its entirety. For example, a kit can be provided including the clot-capturing device as disclosed herein, as well as a coupling mechanism for engaging the device and a distal end of a cannula. The coupling mechanism may be an adhesive mechanism or a mechanical component, or any other coupling methods and devices known in the art, to provide substantially fluid-tight communication between the device and the cannula. The distal end of the cannula may be attached to the exit end of the device.

Although references have been made in connection with surgical protocols, it should be appreciated that the devices, systems and methods of the present invention can be adapted for use in connection with non-surgical protocols, devices and systems, and in connection with any vessel capable of permitting fluid flow therethrough and capable of being obstructed. For instance, the system of the present invention can be adapted for use in connection with clearing obstructed oil pipelines, water pipes, and air ducts, among others.

While the present invention has been described with reference to certain embodiments thereof, it should be understood by those skilled in the art that various changes can be made and equivalents can be substituted without departing from the true spirit and scope of the invention. In addition, many modifications can be made to adapt to a particular situation, indication, material and composition of matter, process step or steps, without departing from the spirit and scope of the present invention.

What is claimed is:

1. A system for capturing undesirable material, the system comprising:
    a first cannula having a distal end, an opposing proximal end, and a pathway extending from the distal end to the proximal end, the distal end of the first cannula having an inflatable body having an entry end, an exit end, and a pathway extending substantially axially through the inflatable body upon inflation, the inflatable body having a first wall layer and a second wall layer, the proximal end of first cannula capable of being in fluid communication to a pump;
    a second cannula in fluid communication with the pump and being designed to have its distal end situated in spaced relation to the distal end of the first cannula,
    a network of veins incorporated into the inflatable body, the network of veins are located between the first wall layer and the second wall layer, and which, upon introduction of a fluid thereinto, inflate the inflatable body to a predetermined shape such that the entry end has a larger diameter than the exit end; and
    the first wall layer and second wall layer both comprised of impermeable material, the network of veins having a plurality of intersections with spaces between each vein, the space between each vein comprises only the first wall layer and the second wall layer.

2. The device of claim 1, wherein the inflatable body is substantially frustoconical upon inflation.

3. The device of claim 1, wherein the veins are interconnected, wherein the first wall layer is bonded to the second wall layer in the space between each vein.

4. The device of claim 1, wherein the wall is substantially inelastic or semi-elastic to maintain the inflatable body in the predetermined shape upon inflation.

5. The device of claim 1, further comprising an elastic sheath for maintaining the inflatable body in a collapsed state before inflation.

6. A method for capturing undesirable material, the method comprising:
    providing the system of claim 1;
    positioning the inflatable body at a site of interest adjacent to the undesirable material;
    introducing a fluid into the network of veins to inflate the inflatable body to the predetermined shape having the entry end, the exit end, and the pathway extending substantiality axially; and
    suctioning the undesirable material through the pathway from the entry end to the exit end and along the pathway of the first cannula.

7. The method of claim 6, wherein in the providing step, the veins are interconnected, wherein the first wall layer is bonded to the second wall layer in the space between each vein.

* * * * *